(12) United States Patent
Herold et al.

(10) Patent No.: US 7,723,550 B2
(45) Date of Patent: May 25, 2010

(54) PROCESS FOR PREPARING ORGANIC COMPOUNDS

(75) Inventors: Peter Herold, Allschwil (CH); Robert Mah, Allschwil (CH); Stefan Stutz, Allschwil (CH); Aleksandar Stojanovic, Allschwil (CH); Isabelle Lyothier, Allschwil (CH); Dirk Behnke, Allschwil (CH)

(73) Assignee: Novartis AG, Basel (CH)

( * ) Notice: Subject to any disclaimer, the term of this patent is extended or adjusted under 35 U.S.C. 154(b) by 75 days.

(21) Appl. No.: 12/224,418

(22) PCT Filed: Nov. 8, 2007

(86) PCT No.: PCT/EP2007/062024

§ 371 (c)(1),
(2), (4) Date: Aug. 27, 2008

(87) PCT Pub. No.: WO2008/055941

PCT Pub. Date: May 15, 2008

(65) Prior Publication Data

US 2009/0105503 A1      Apr. 23, 2009

(30) Foreign Application Priority Data

Nov. 8, 2006 (EP) .................. 06123706

(51) Int. Cl.
*C07C 29/36* (2006.01)
*C07C 29/44* (2006.01)
*C07C 41/18* (2006.01)
*C07C 41/30* (2006.01)
*C07C 43/23* (2006.01)

(52) U.S. Cl. ...................... 568/813; 564/170
(58) Field of Classification Search ........................ None
See application file for complete search history.

(56) References Cited

U.S. PATENT DOCUMENTS

| 4,937,373 | A | 6/1990 | Carson et al. | |
| 6,800,769 | B2 * | 10/2004 | Stutz et al. | 552/11 |
| 2004/0092766 | A1 | 5/2004 | Stutz et al. | |

FOREIGN PATENT DOCUMENTS

WO         02/02487      1/2002

OTHER PUBLICATIONS

International Search Report dated Mar. 28, 2008 in the International (PCT) Application PCT/EP2007/062024 of which the present application is the U.S. National Stage.
PCT Written Opinion dated Mar. 28, 2008 in the International (PCT) Application PCT/EP2007/062024 of which the present application is the U.S. National Stage.
Maximilian A. Silvestri et al., "Design, Synthesis, Anti-HIV Activities, and Metabolic Stabilities of Alkenyldiarylmethane (ADAM) Non-nucleoside Reverse Transcriptase Inhibitors", J. Med. Chem., vol. 47, No. 12, pp. 3149, 3152 and 3159, XP002468984, 2004.
Christine Gottardo et al., "Palladium-catalyzed carbon-carbon coupling reactions using aryl Grignards", Tetrahedron Letters, vol. 43, No. 39, pp. 7097-7094, XP004378307, ISSN: 0040-4039, 2002.
J.G. Duboudin et al., "Gamma Functional vinyl Grignard reagents. I. Reactivity of organomagnesium compounds with alpha-acetylenic alcohols in the presence of copper halides", Journal of Organometallic Chemistry, vol. 168, No. 1, pp. 1-11, XP002028213, 1979.
Lars-Inge Olsson et al., "Addition Reactions of Butyllithium with Propargylic Alcohols", Tetrahedron Letters, vol. 15, No. 25, pp. 2161-2162, XP002430643, 1974.
Fuk Yee Kwong et al., "Iridium-catalyzed cascade decarbonylation/ highly enantioselective Pauson-Khand-type cyclization reactions", Tetrahedron: Asymmetry, 17, pp. 1238-1252, 2006.
Jay Wrobel et al., "Novel 5-(3-Aryl-2-propyny1)-5-(arylsulfonyl)thiazolidine-2,4-diones as Antihyperglycemic Agents", J. Med. Chem., vol. 41, pp. 1084-1091, XP001124338, 1998.
N.A. Bumagin et al., "A Convenient Synthesis of Substituted Propargyl Alcohols and Terminal Acetylenes", Synthesis Communications, pp. 728-729, XP002417737, Sep. 1984.

(Continued)

*Primary Examiner*—Brian J Davis
(74) *Attorney, Agent, or Firm*—Wenderoth, Lind & Ponack, L.L.P.

(57) ABSTRACT

Process for preparing a compound of the formula (I) in which $R_1$ and $R_2$ are each independently H, $C_1$-$C_8$-alkyl, halogen, polyhalo-$C_1$-$C_8$-alkoxy, polyhalo-$C_1$-$C_8$-alkyl, $C_1$-$C_8$-alkoxy, $C_1$-$C_8$-alkoxy-$C_1$-$C_8$-alkyl, or $C_1$-$C_8$-alkoxy-$C_1$-$C_8$-alkoxy, where $R_1$ and $R_2$ are not both H, and $R_3$ is $C_1$-$C_8$-alkyl, which is characterized in that a) a compound of the formula (II) in which $R_1$ and $R_2$ are each as defined above and X is Br, I, triflate, toyslate or mesylate is reacted with prop-2-yn-1-ol to give the compound of the formula (III), b) the compound of the formula (III) is reacted with an alkyl-metal compound in which "alkyl" is as defined above for $R_3$ to give a compound of the formula (I).

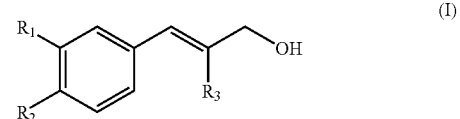

(I)

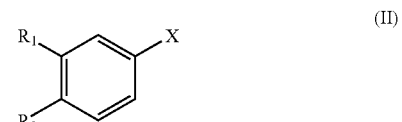

(II)

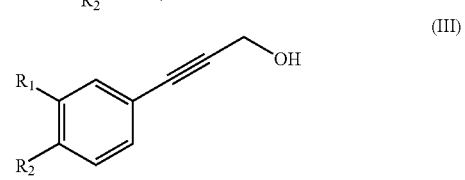

(III)

9 Claims, No Drawings

OTHER PUBLICATIONS

Adelheid Godt, "Synthesis of Unsymmetrical 1,4-Diarylbutadiynes by Stille Coupling", J. Org. Chem., vol. 62, pp. 7471-7474, XP002402972, 1997.

Yun Liang et al., "Modified Palladium-Catalyzed Sonogashira Cross-Coupling Reactions under Copper-, Amine-, and Solvent-Free Conditions", J. Org. Chem., vol. 71, pp. 379-381, XP002430644, 2006.

Alexander V. Muehldorf et al., "The Enantiospecific Nicholas Reaction", Tetrahedron Letters, vol. 35, No. 47, pp. 8755-8758, XP002430645, 1994.

Beilstein Registry No. 9554952, XP002430651, 2003.

Beilstein Registry No. 2099478, XP002430652, 1973.

Guo-Hua Fang et al., "The First Preparation of 4-Substituted 1,2-Oxaborol-2(5H)-ols and their Palladium-Catalyzed Cross-Coupling with Aryl Halides to Prepare Stereodefined 2,3-Disubstituted Allyl Alcohols", Synthesis, No. 7, pp. 1148-1154, XP002430646, 2006.

\* cited by examiner

PROCESS FOR PREPARING ORGANIC COMPOUNDS

FIELD OF THE INVENTION

The invention relates to a stereoselective process for preparing (E)-2-alkyl-3-aryl-prop-2-en-1-ol and to novel intermediates which are obtained in the process stages.

BACKGROUND OF THE INVENTION

EP-A-0 678 503 describes delta-amino-gamma-hydroxy-omega-aryl-alkanecarboxamides which have renin-inhibiting properties and can be used as antihypertensives in pharmaceutical formulations. The preparation processes described there are unsuitable for an industrial process, especially with regard to the sometimes unsatisfactory yields and number of reaction steps. A great disadvantage of the processes described there is that the total yield of pure diastereomers is too low.

An improved preparation process for delta-amino-gamma-hydroxy-omega-aryl-alkanecarboxamides has been described in WO 2002/02487 A1. In the process described there, arylaldehydes are reacted with 2-alkylacetic esters to give 3-hydroxy-2-alkyl-3-arylpropionic esters, from which conversion of the alcohol function to a leaving group followed by elimination affords 2-alkyl-3-arylacrylic esters, which are reduced to (E)-2-alkyl-3-arylprop-2-en-1-ols, which are then hydrogenated by asymmetric hydrogenation with high stereoselectivity to chiral 2-methyl-3-phenyl-propan-1-ols. The chiral 2-methyl-3-phenylpropan-1-ols are subsequently converted by hydrogenation to (3-halo-2-alkylpropyl)aryl compounds, which are reacted with chiral (E)-5-halo-2-alkylpent-4-enamides to give 2,7-dialkyl-8-aryl-4-octenoylamides. The double bond of the 2,7-dialkyl-8-aryl-4-octenoylamides is subsequently halogenated simultaneously in the 5-position and hydroxylated with lactonization in the 4-position, then the halide is replaced with azide, the lactone is amidated and then the azide is converted to the amine group. The desired alkanecarboxamides are obtained in significantly higher overall yields in this process compared to the process published in EP-A-0 678 503, although the high number of process stages is disadvantageous.

DETAILED DESCRIPTION OF THE INVENTION

In a novel process, the starting materials are 2,7-dialkyl-8-aryl-4-octenoylamides, which are prepared by a novel, more efficient and shorter route.

The 2,7-dialkyl-8-aryl-4-octenoylamides may, for example, correspond to the formula A

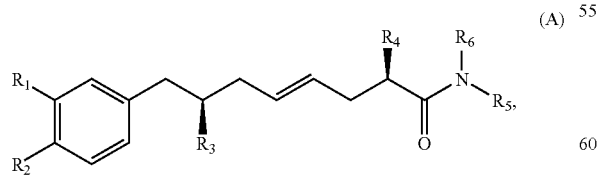

(A)

in which $R_1$ and $R_2$ are each independently H, $C_1$-$C_8$-alkyl, halogen, polyhalo-$C_1$-$C_8$-alkoxy, polyhalo-$C_1$-$C_8$-alkyl, $C_1$-$C_8$-alkoxy, $C_1$-$C_8$-alkoxy-$C_1$-$C_8$-alkyl or $C_1$-$C_8$-alkoxy-$C_1$-$C_8$-alkoxy, where $R_1$ and $R_2$ are not both H, $R_3$ is $C_1$-$C_8$-alkyl, $R_4$ is $C_1$-$C_8$-alkyl, $R_5$ is $C_1$-$C_8$-alkyl or $C_1$-$C_8$-alkoxy, $R_6$ is $C_1$-$C_8$-alkyl, or $R_5$ and $R_6$ together are optionally $C_1$-$C_4$-alkyl-, phenyl- or benzyl-substituted tetramethylene, pentamethylene, 3-oxa-1,5-pentylene or —CH$_2$CH$_2$O—C(O)—.

The compounds of the formula A are obtained analogously to the process described in WO 2002/02487 A1, by reacting a compound of the formula B

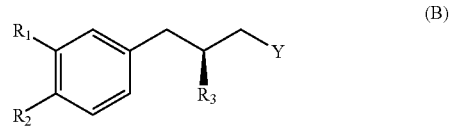

(B)

with a compound of the formula C

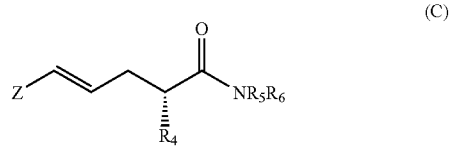

(C)

in which $R_1$ to $R_6$ are each as defined above, Y is Cl, Br or I and Z is Cl, Br or I, in the presence of an alkali metal or alkaline earth metal. Y and Z are preferably each Br or Cl and more preferably Cl.

The compounds of the formula C can be prepared by amidating or transamidating the corresponding carboxylic esters, carboxamides or carbonyl halides. The formation of carboxamides from carboxylic esters and amines in the presence of trialkylaluminium or dialkylaluminium halide, for example with trimethylaluminium or dimethylaluminium chloride, is described by S. M. Weinreb in *Organic Syntheses*, 59, pages 49-53 (1980). The carboxylic esters are obtainable by the reaction of trans-1,3-dihalopropene (for example trans-1,3-dichloropropene) with corresponding carboxylic esters in the presence of strong bases, for example alkali metal amides.

The compounds of the formula B may, analogously to the process described in WO 2002/02487 A1, be prepared by halogenation from 2-alkyl-3-aryl-1-propanols of the formula D. The virtually enantiomerically pure 2-alkyl-3-aryl-1-propanols of the formula D can be prepared by enantioselective hydrogenation of the corresponding (E)-allyl alcohols.

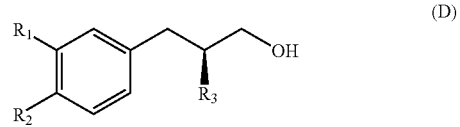

(D)

In a specific embodiment, the compound of the formula B is an important intermediate (known under the name "Synthon A") in the commercially employed synthesis of aliskiren (also known under the name SPP100), the active ingredient of the renin inhibitor recently approved in the USA under the name Tekturna®. The preparation of this renin inhibitor per se constituted an extremely complex task for the technical field (W. Wolfson, *Chemistry & Biology*, 13, pages 1119-1120 (2006)).

It has now been found that, surprisingly, (E)-2-alkyl-3-arylprop-2-en-1-ols of the formula (I) below, which are key intermediates for the novel preparation process mentioned at the outset proceeding from 2,7-dialkyl-8-aryl-4-octenoylamides, can be prepared in high yields in only two process stage: when suitably substituted, unsaturated aromatic bromides, iodides, or else triflates, tosylates or mesylates, are reacted with prop-2-yn-1-ol to give 3-arylprop-2-yn-1-ols, the products are obtained in high yields. This is unexpected since, for example, C. Gottardo in *Tetrahedron Letters*, 43, pages 7091-7094 (2002) ((Section 2) and (Table 1)) and M. Cushman in *Journal of Medicinal Chemistry* 47, pages 3149-3162 (2004) (conversion of compound 52 to compound 53) state and demonstrate that aryl halides which have electron donor substituents (especially in the meta-position) are significantly less reactive in cross-coupling reactions than unsubstituted aryl halides or aryl halides with electron-withdrawing substituents.

The 3-arylprop-2-yn-1-ols are an important intermediate of the process. Proceeding from these 3-arylprop-2-yn-1-ols, the (E)-2-alkyl-3-arylprop-2-en-1-ols are obtained in high yields by reaction with an alkyl-metal compound.

Processes similar to the first process stage for 1-arylprop-2-yne compounds are described in the literature by S. Bhattacharya and S. Sengupta in *Tetrahedron Letters*, Vol. 45 (2004), pages 8733-8736. Moreover, processes similar to the second process stage for 2-alkyl-3-phenylprop-2-en-1-ol compounds are described in the literature by J. G. Duboudin and B. Jousseaume in *Journal of Organometallic Chemistry*, Vol. 168 (1979), pages 1-11, or A. Claesson in *Tetrahedron Letters*, Vol. (1974), pages 2161-2162.

Compared to the process known from WO 2002/02487 A1 for preparing delta-amino-gamma-hydroxy-omega-arylalkanecarboxamides, this novel process is notable in that it is significantly shorter and that reaction steps which have to be performed at temperatures below −10° C. are avoided, which is practically and financially advantageous for preparation on the industrial scale.

The invention provides a process for preparing a compound of the formula

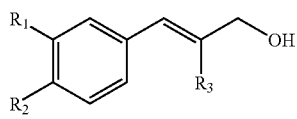

(I)

in which $R_1$ and $R_2$ are each independently H, $C_1$-$C_8$-alkyl, halogen, polyhalo-$C_1$-$C_8$-alkoxy, polyhalo-$C_1$-$C_8$-alkyl, $C_1$-$C_8$-alkoxy, $C_1$-$C_8$-alkoxy-$C_1$-$C_8$-alkyl, or $C_1$-$C_8$-alkoxy-$C_1$-$C_8$-alkoxy, where $R_1$ and $R_2$ are not both H, and $R_3$ is $C_1$-$C_8$-alkyl, which is characterized in that a) a compound of the formula

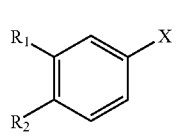

(II)

in which $R_1$ and $R_2$ are each as defined above and X is Br, I, triflate, toyslate or mesylate is reacted with prop-2-yn-1-ol to give the compound of the formula

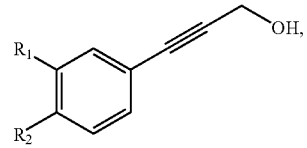

(III)

and b) the compound of the formula (III) is reacted with an alkyl-metal compound in which "alkyl" is as defined above for $R_3$ to give a compound of the formula (I).

$R_1$ and $R_2$ may, as $C_1$-$C_8$-alkyl, be linear or branched and preferably contain 1 to 4 carbon atoms. Examples are methyl, ethyl, n- and i-propyl, n-, i- and t-butyl, pentyl and hexyl.

$R_1$ and $R_2$ may, as polyhalo-$C_1$-$C_8$-alkyl, be linear or branched and preferably contain 1 to 4, more preferably 1 or 2 carbon atoms. Examples are fluoromethyl, difluoromethyl, trifluoromethyl, chloromethyl, dichloromethyl, trichloromethyl, 2-chloroethyl and 2,2,2-trifluoroethyl.

$R_1$ and $R_2$ may, as polyhalo-$C_1$-$C_8$-alkoxy, be linear or branched and preferably contain 1 to 4, more preferably 1 or 2 carbon atoms. Examples are fluoromethoxy, difluoromethoxy, trifluoromethoxy, chloromethoxy, dichloromethoxy, trichloromethoxy, 2-chloroethoxy and 2,2,2-trifluoroethoxy.

$R_1$ and $R_2$ may, as halogen, including halogen in polyhalo-$C_1$-$C_8$-alkyl and polyhalo-$C_1$-$C_8$-alkoxy, be F, Cl or Br, preference being given to F and Cl.

$R_1$ and $R_2$ may, as $C_1$-$C_8$-alkoxy, be linear or branched and preferably contain 1 to 4 carbon atoms. Examples are methoxy, ethoxy, n- and i-propoxy, n-, i- and t-butoxy, pentoxy and hexoxy.

$R_1$ and $R_2$ may, as $C_1$-$C_8$-alkoxy-$C_1$-$C_8$-alkyl, be linear or branched. The alkoxy group contains preferably 1 to 4 and particularly 1 or 2 carbon atoms, and the alkyl group contains preferably 1 to 4 carbon atoms. Examples are methoxymethyl, 1-methoxy-eth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propoxymethyl, butoxymethyl, 1-propoxyeth-2-yl and 1-butoxyeth-2-yl.

$R_1$ and $R_2$ may, as $C_1$-$C_8$-alkoxy-$C_1$-$C_8$-alkoxy, be linear or branched. The alkoxy group contains preferably 1 to 4 and particularly 1 or 2 carbon atoms, and the alkoxy group contains preferably 1 to 4 carbon atoms. Examples are methoxymethoxy, 2-methoxyethoxy, 3-methoxypropoxy, 4-methoxybutoxy, methoxypentoxy, methoxyhexoxy, ethoxymethoxy, 2-ethoxyethoxy, 3-ethoxypropoxy, 4-ethoxybutoxy, ethoxypentoxy, ethoxyhexoxy, propoxymethoxy, butoxymethoxy, 2-propoxyethoxy and 2-butoxyethoxy.

The compound groups mentioned above and below are not to be regarded as closed, but rather parts of these compound groups may be exchanged with one another or with the definitions given above or omitted in a sensible manner, for example to replace general by more specific definitions. The definitions are valid in accordance with general chemical principles, such as, for example, the common valences for atoms.

In a preferred embodiment, $R_1$ is a $C_1$-$C_8$-alkoxy-$C_1$-$C_8$-alkoxy radical and $R_2$ is a $C_1$-$C_8$-alkyl radical or a $C_1$-$C_8$-alkoxy radical.

In a further preferred embodiment, $R_1$ is a $C_1$-$C_4$-alkoxy-$C_1$-$C_4$-alkoxy radical and $R_2$ is a $C_1$-$C_4$-alkyl radical or a $C_1$-$C_4$-alkoxy radical.

In a further preferred embodiment, $R_1$ is methoxy- or ethoxy-$C_1$-$C_4$-alkoxy, and $R_2$ is preferably methyl, ethyl, methoxy or ethoxy.

Particular preference is given to compounds of the formula (I) in which $R_1$ is 3-methoxypropoxy or 4-methoxybutoxy and $R_2$ is methyl or methoxy.

Very particular preference is given to compounds of the formula (I) in which $R_1$ is 3-methoxypropoxy and $R_2$ is methoxy.

$R_3$ may, as $C_1$-$C_8$-alkyl, be linear or branched and preferably contain 1 to 4 carbon atoms. Examples are methyl, ethyl, n- and i-propyl, n-, i- and t-butyl, pentyl and hexyl. In a preferred embodiment, $R_3$ in the compounds of the formula (I) is isopropyl.

In a further preferred embodiment, $R_1$ is a $C_1$-$C_8$-alkoxy-$C_1$-$C_8$-alkoxy radical, $R_2$ is a $C_1$-$C_8$-alkyl radical or a $C_1$-$C_8$-alkoxy radical and $R_3$ is isopropyl.

In a further preferred embodiment, $R_1$ is a $C_1$-$C_4$-alkoxy-$C_1$-$C_4$-alkoxy radical, $R_2$ is a $C_1$-$C_4$-alkyl radical or a $C_1$-$C_4$-alkoxy radical and $R_3$ is isopropyl.

A very particularly preferred embodiment is the compound of the formula (I) in which $R_1$ is 3-methoxypropoxy, $R_2$ is methoxy and $R_3$ is isopropyl.

The starting compounds of the formula II used in process stage a) (X=Br, I) are known or can be prepared analogously to known processes. The starting compounds of the formula II (X=triflate, tosylate, mesylate) are obtainable from the corresponding phenols analogously to known processes.

Process stage a) is advantageously performed at relatively high temperatures, for example 60 to 90° C., in the presence of catalytic amounts of palladium catalyst, for example $Pd(PPh_3)_4$ or $Pd(PPh_3)_2Cl_2$ or $Pd/C+PPh_3$, and optionally catalytic amounts of a copper(I) halide, for example CuI, and in the presence of at least equivalent amounts of an amine base. The reaction is also appropriately performed without solvent, but can also be performed in polar protic solvents, for example water. Suitable amine bases are, for example, piperidine, pyrrolidine, diisopropylethylamine, triethylamine or ammonia.

The addition in process stage b) is advantageously performed at relatively low temperatures, for example –10° C. to room temperature (e.g. 23° C.), in the presence of catalytic amounts of a copper(I) halide, for example CuI. The alkylmetal compound is advantageously used in excess. The reaction can optionally be performed in the presence of an additive, for example TMEDA. The reaction is also appropriately performed in a solvent in which the compounds of the formula (III) are readily soluble, and ethers, for example diethyl ether, tetrahydrofuran and dioxane, are suitable. Tetrahydrofuran and dioxane are particularly suitable.

Preferred alkyl-metal compounds are alkylmagnesium halides where "halide" is Br or Cl.

The reaction of process stage b) proceeds regiospecifically and leads virtually exclusively to the desired products of the formula (I).

The regiospecific process according to the invention can be used to prepare the intermediates for preparing the delta-amino-gamma-hydroxy-omega-arylalkane-carboxamides in high yields over all process stages. The high overall yields make the process suitable for industrial use.

The invention also provides the compound (intermediate) of the formula

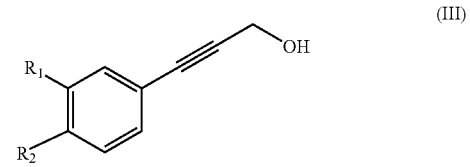

in which $R_1$ is methoxypropoxy, and $R_2$ is methoxy.

The invention also provides a process according to claim 1, wherein the compound of the formula (I) prepared according to claim 1 is converted by asymmetric hydrogenation to a compound of the formula D

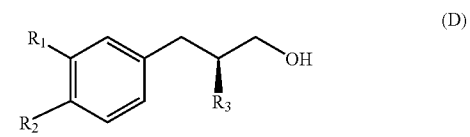

in which $R_1$ is a linear or branched $C_1$-$C_8$-alkoxy-$C_1$-$C_8$-alkoxy radical, $R_2$ is a linear or branched $C_1$-$C_8$-alkyl radical or a linear or branched $C_1$-$C_8$-alkoxy radical, and $R_3$ is isopropyl, the compound of the formula D is converted by halogenation to a compound of the formula B

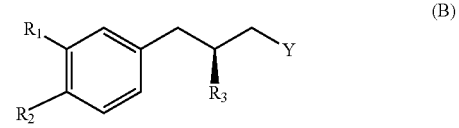

where Y is Cl, Br or I, and the compound of the formula B is reacted with a compound of the formula C,

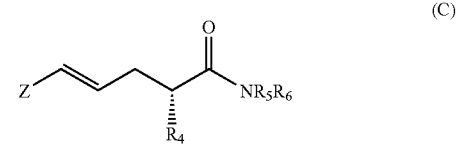

in which $R_4$ is $C_1$-$C_8$-alkyl, $R_5$ is $C_1$-$C_8$-alkyl or $C_1$-$C_8$-alkoxy, $R_6$ is $C_1$-$C_8$-alkyl, or $R_5$ and $R_6$ together are optionally $C_1$-$C_4$-alkyl-, phenyl- or benzyl-substituted tetramethylene, pentamethylene, 3-oxa-1,5-pentylene or —$CH_2CH_2O$—C(O)—, and Z is Cl, Br or I, in the presence of an alkali metal or alkaline earth metal, to give a compound of the formula A

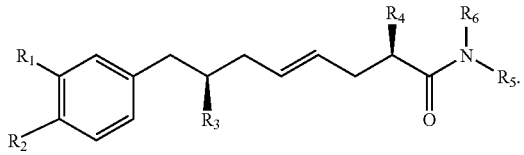

(A)

For $R_1$, $R_2$ and $R_3$, the embodiments and preferences described above apply.

In a preferred embodiment, $R_1$ is methoxy- or ethoxy-$C_1$-$C_4$-alkoxy, and $R_2$ is preferably methyl, ethyl, methoxy or ethoxy.

The examples which follow illustrate the invention in detail.

EXAMPLES

HPLC gradient on Hypersil BDS C-18 (5 μm); column: 4×125 mm
(I) 90% water*/10% acetonitrile* to 0% water*/100% acetonitrile* in 5 minutes+2.5 minutes (1.5 ml/min)
(II) 95% water*/5% acetonitrile* to 0% water*/100% acetonitrile* in 40 minutes (0.8 ml/min)
contains 0.1% trichloroacetic acid Example A Process for preparing 2-[1-[4-methoxy-3-(3-methoxypropoxy)phenyl]meth-(E)-ylidene]-3-methylbutan-1-ol (A2)

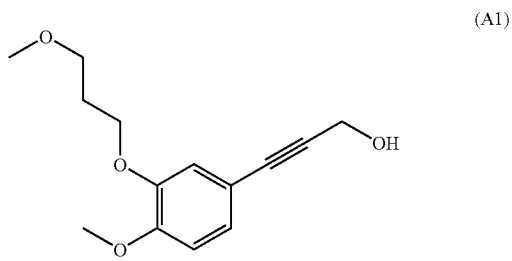

(A1)

Example A1

Preparation of 3-[4-methoxy-3-(3-methoxypropoxy) phenyl]prop-2-yn-1-ol

A 250 ml round-bottom flask is initially charged with 17.991 mmol of 4-bromo-1-methoxy-2-(3-methoxypropoxy) benzene [173336-76-0] and 0.720 mmol of tetrakis(triphenylphosphine)palladium(0), and the apparatus is evacuated under high vacuum for 30 minutes and then charged with argon. 45 ml of pyrrolidine and 35.982 mmol of prop-2-yn-1-ol are added to the reaction vessel and the solution is stirred at 80° C. over 17 hours. The reaction mixture is cooled to room temperature and poured onto 200 ml of saturated aqueous ammonium chloride solution. The mixture is extracted with ethyl acetate (2×350 ml). The combined organic phases are washed with brine (200 ml), dried over sodium sulphate, filtered and concentrated by evaporation on a rotary evaporator. The title compound A1 is obtained as a brown oil (3.96 g) from the residue by means of flash chromatography (SiO$_2$ 60 F, 2:1 ethyl acetate-hexane). Rf=0.21 (1:1 ethyl acetate-heptane); Rt=3.32 (gradient I).

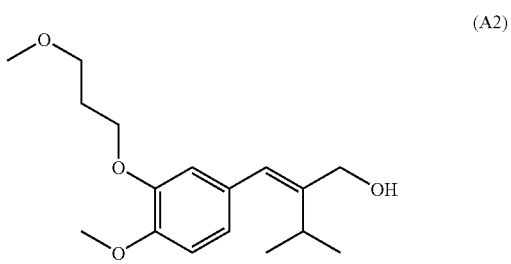

(A2)

Example A2

Preparation of 2-[1-[4-methoxy-3-(3-methoxypropoxy)phenyl]meth-(E)-ylidene]-3-methylbutan-1-ol A dried 50 ml Schlenk tube is charged under an argon atmosphere with a solution of 4.034 mmol of 3-[4-methoxy-3-(3-methoxypropoxy)phenyl]prop-2-yn-1-ol in 20 ml of tetrahydrofuran. The solution is admixed with 0.403 mmol of solid copper(I) iodide and the suspension is cooled to 0° C. Subsequently 6.05 ml of a 2.0 molar isopropyl-magnesium chloride solution in diethyl ether are added. The resulting mixture is stirred at 0° C. over 3.5 hours. The reaction mixture is then poured onto saturated aqueous ammonium chloride solution at 0° C. and then diluted with water and ethyl acetate. The phases are separated; the aqueous phase is extracted with ethyl acetate (2×). The combined organic phases are washed with brine, dried over sodium sulphate, filtered and concentrated by evaporation on a rotary evaporator. The title compound A2 is obtained as a yellow oil (967 mg) from the residue by means of flash chromatography (SiO$_2$ 60 F, 2:1 ethyl acetate-hexane). Rf=0.48 (2:1 ethyl acetate-heptane); Rt=3.97 (gradient I).

The invention claimed is:

1. Process for preparing a compound of the formula I

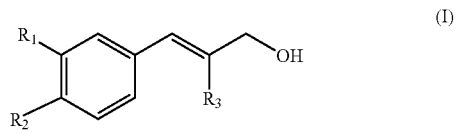

(I)

in which $R_1$ is a linear or branched $C_1$-$C_8$-alkoxy-$C_1$-$C_8$-alkoxy radical, $R_2$ is a linear or branched $C_1$-$C_8$-alkyl radical or a linear or branched $C_1$-$C_8$-alkoxy radical, and $R_3$ is isopropyl, which is characterized in that
a) a compound of the formula II

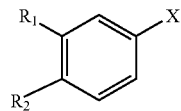
(II)

in which $R_1$ and $R_2$ are each as defined above and X is Br, I, triflate, toyslate or mesylate is reacted with prop-2-yn-1-ol to give the compound of the formula III

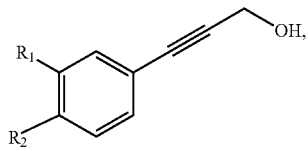
(III)

b) the compound of the formula III is reacted with an alkyl-metal compound in which "alkyl" is as defined above for $R_3$ to give a compound of the formula I.

2. Process according to claim 1, wherein $R_1$ is methoxy- or ethoxy-$C_1$-$C_4$-alkoxy, and $R_2$ is methyl, ethyl, methoxy or ethoxy.

3. Process according to claim 1, wherein $R_1$ is 3-methoxypropoxy or 4-methoxybutoxy and $R_2$ is methyl or methoxy.

4. Process according to claim 1, wherein $R_1$ is 3-methoxypropoxy and $R_2$ is methoxy.

5. Compound of the formula III

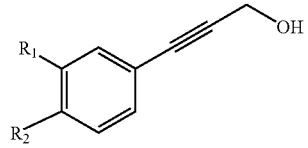
(III)

in which $R_1$ is methoxypropoxy, and $R_2$ is methoxy.

6. Process according to claim 1, wherein the compound of the formula (I) prepared according to claim 1 is converted by asymmetric hydrogenation to a compound of the formula D

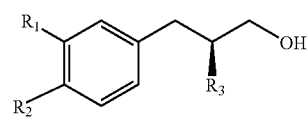
(D)

in which
$R_1$ is a linear or branched $C_1$-$C_8$-alkoxy-$C_1$-$C_8$-alkoxy radical,
$R_2$ is a linear or branched $C_1$-$C_8$-alkyl radical or a linear or branched $C_1$-$C_8$-alkoxy radical, and
$R_3$ is isopropyl,
the compound of the formula D is converted by halogenation to a compound of the formula B

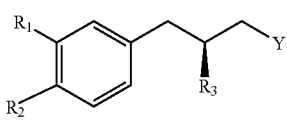
(B)

where Y is Cl, Br or I,
the compound of the formula B is reacted with a compound of the formula C,

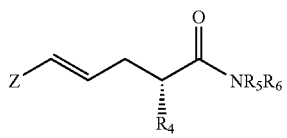
(C)

in which $R_4$ is $C_1$-$C_8$-alkyl, $R_5$ is $C_1$-$C_8$-alkyl or $C_1$-$C_8$-alkoxy, $R_6$ is $C_1$-$C_8$-alkyl, or $R_5$ and $R_6$ together are optionally $C_1$-$C_4$-alkyl-, phenyl- or benzyl-substituted tetramethylene, pentamethylene, 3-oxa-1,5-pentylene or —$CH_2CH_2O$—$C(O)$—, and Z is Cl, Br or I,
in the presence of an alkali metal or alkaline earth metal, to give a compound of the formula A

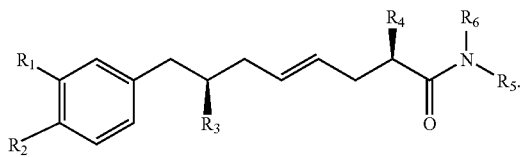
(A)

7. Process according to claim 6, wherein $R_1$ is methoxy- or ethoxy-$C_1$-$C_4$-alkoxy, and $R_2$ is methyl, ethyl, methoxy or ethoxy.

8. Process according to claim 6, wherein $R_1$ is 3-methoxypropoxy or 4-methoxybutoxy and $R_2$ is methyl or methoxy.

9. Process according to claim 6, wherein $R_1$ is 3-methoxypropoxy and $R_2$ is methoxy.

* * * * *